(12) United States Patent
Caricofe

(10) Patent No.: US 6,265,449 B1
(45) Date of Patent: Jul. 24, 2001

(54) AQUEOUS COMPOSITIONS COMPRISING RANITIDINE AND LCMT SUCROSE

(75) Inventor: Ralph Boyer Caricofe, Raleigh, NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/445,668

(22) PCT Filed: Jul. 22, 1998

(86) PCT No.: PCT/EP98/04503

§ 371 Date: Dec. 10, 1999

§ 102(e) Date: Dec. 10, 1999

(87) PCT Pub. No.: WO99/04788

PCT Pub. Date: Feb. 4, 1999

(30) Foreign Application Priority Data

Jul. 23, 1997 (GB) .................................... 9715423

(51) Int. Cl.⁷ ........................ A61K 31/135; A61K 31/70
(52) U.S. Cl. ............................................... 514/653; 514/23

(58) Field of Search ........................................ 514/23, 653

(56) References Cited

U.S. PATENT DOCUMENTS

| | | | | |
|---|---|---|---|---|
| 4,585,790 | * | 4/1986 | Padfield et al. | 514/471 |
| 5,068,249 | * | 11/1991 | Long | 514/471 |
| 5,456,918 | * | 10/1995 | Quirk et al. | 424/51 |
| 5,593,685 | * | 1/1997 | Bye et al. | 424/439 |

FOREIGN PATENT DOCUMENTS

| | | |
|---|---|---|
| 2 142 820 | 1/1985 | (GB) . |
| 2 198 352 | 6/1988 | (GB) . |
| WO 94 08560 | 4/1994 | (WO) . |

* cited by examiner

*Primary Examiner*—KEvin E. Weddington
(74) *Attorney, Agent, or Firm*—Lorie Ann Morgan

(57) ABSTRACT

The invention relates to an aqueous pharmaceutical composition for oral administration comprising ranitidine, or a pharmaceutically acceptable salt thereof, characterized in that the composition contains low color, metal, turbidity (LCMT) sucrose.

8 Claims, No Drawings

AQUEOUS COMPOSITIONS COMPRISING RANITIDINE AND LCMT SUCROSE

This application is filed pursuant to 35 U.S.C. §371 as a United States National Phase Application of International Application No. PCT/EP98/04503 filed Jul. 22, 1998, which claims priority from GB9715423.1 filed Jul. 23, 1997.

The present invention relates to aqueous compositions containing the histamine $H_2$-receptor antagonist ranitidine.

Ranitidine, N-[2-[[[5-(dimethylamino)methyl-2-furanyl]methyl]thio]ethyl]-N'-methyl-2-nitro-1,1-ethenediamine, and its pharmaceutically acceptable salts are described and claimed in British Patent Specification No. 1565966 and a particular crystalline form of ranitidine hydrochloride is described and claimed in British Patent Specification No. 2084580. In both these specifications there is reference to formulations for oral administration, which may take the form of for example tablets, capsules, granules, powders, solutions, syrups, suspensions, or tablets, or lozenges for buccal administration. Oral administration constitutes a preferred route for administering ranitidine.

Oral administration in the form of a conventional tablet, pill or capsule constitutes a preferred route for administration of pharmaceuticals since this route is generally convenient and acceptable to patients. Unfortunately such compositions may be associated with certain disadvantages, particularly in the treatment of pediatric or geriatric patients, who may dislike or have difficulty in swallowing such compositions, or where administration of a conventional tablet, pill or capsule is not feasible. In such situations, oral liquid compositions are often preferable. It is highly desirable, particularly in the treatment of acute conditions, that pharmaceutical compositions have a rapid and consistent onset of action combined with sustained activity and good bioavailability.

Oral liquid compositions containing ranitidine are described in British Patent Specification No. GB 2142820 which describes aqueous based compositions containing ranitidine and/or one or more of its pharmaceutically acceptable salts, having a pH within the range 6.5–7.5.

Also, British Patent Specification No. GB 2198352 describes aqueous ranitidine compositions with enhanced stability due to the addition of ethanol within the range of 2.5–10% weight/volume of the complete composition.

Ranitidine, in common with many drug substances, has an inherently bitter taste, and this constitutes a disadvantage with existing oral liquid compositions, for example those described in GB 2142820 and GB 2198352. Moreover, it is well known that patients may not complete a necessary course of medicine if they are prescribed an oral presentation which is particularly unpleasant to taste. The problems resulting from the bitter taste of ranitidine are particularly acute in formulations such as oral liquids.

A high proportion of alcohol in an oral liquid pharmaceutical composition is not desirable, especially if the composition is to be self-administered by the patient or is to be available "over the counter" (OTC) without prescription. An oral liquid composition of ranitidine which achieves good stability without the need for high concentrations of alcohol is therefore desirable.

Surprisingly, it has now been found that the use of low colour, metal, turbidity (LCMT) sucrose in an aqueous ranitidine composition for oral administration results in improved stability, bioavailability and taste-masking of ranitidine whilst allowing the volume of alcohol required in the solution to be reduced.

Thus, the present invention provides an aqueous composition for oral administration comprising ranitidine, or a pharmaceutically acceptable salt thereof, characterised in that the composition contains low colour metal, turbidity (LCMT) sucrose.

Low colour, metal, turbidity (LCMT) sucrose is a special grade of sucrose characterised in that it contains a reduced proportion of impurities compared to N.F. sucrose. LCMT sucrose is available from the Domino Sugar Corporation, New York.

The compositions according to the invention may be in the form of liquids, suspensions or syrups. Preferably the compositions are formulated as liquids.

The amount of LCMT sucrose present in the composition according to the invention is preferably in the range of 5 to 60% w/v based on the complete formulation, more especially about 45% w/v.

The stability of the composition may be further enhanced by the addition of low levels of ethanol, thus, according to a further aspect, the invention provides an aqueous composition for oral administration comprising ranitidine, or a pharmaceutically acceptable salt thereof, LCMT sucrose and ethanol.

Preferably the amount of ethanol in the composition on a weight/volume basis of the complete formulation, is within the range 4 to 5.5% and more particularly is 4.75%.

The stability of the composition may be further enhanced by adjusting the pH of the solution.

The required pH of the composition is preferably obtained by the use of suitable buffer salts for example, citric acid and disodium hydrogen orthophosphate or, preferably potassium dihydrogen orthophosphate and disodium hydrogen orthophosphate.

Preferred compositions according to the invention are those in which the pH of the aqueous composition is within the range 6.8 to 7.4, particularly with a pH of 7.1.

Thus, according to a further aspect, the invention provides an aqueous composition for oral administration comprising ranitidine, or a pharmaceutically acceptable salt thereof, LCMT sucrose, ethanol and a suitable buffer system.

The pharmaceutical compositions according to the invention may also contain other excipients conventional to the art such as flavouring aids, preservatives, viscosity enhancing agents, colouring aids, additional sweeteners, and mixtures thereof.

The flavouring in the liquid according to the invention is preferably a strong flavouring such as fruit flavours and natural or synthetic mint or peppermint flavours. Strong mint or peppermint flavourings are preferred.

Suitable preservatives include one or more alkyl hydroxybenzoates such as methyl, ethyl, propyl and/or butyl hydroxybenzoates and mixtures thereof. Preferably the compositions according to the invention include propyl and/or butylparaben.

Suitable viscosity enhancing agents include gums (e.g. Xanthan gum); sorbitol; glycerol; polyvinyl alcohol; polyvinylpyrrolidine; cellulose derivatives, such as carboxymethylcellulose or a salt thereof, $C_{1-4}$alkyl and/or hydroxy $C_{2-4}$alkyl ether of cellulose, such as methylcellulose, ethylcellulose, hydroxyethylcellulose, hydroxypropylcellulose, hydroxyethylmethylcellulose and hydroxypropylmethylcellulose; and mixtures thereof. Preferably the viscosity enhancing agent is hydroxypropylmethylcellulose.

Preferably the amount of viscosity enhancing agent (for example, hydroxypropylmethylcellulose) in the composition on a weight/volume basis of the complete formulation is within the range to 5% and more particularly is 0.45%.

Aqueous compositions according to the invention conveniently have a viscosity which lies in the range 1 to 150 cps, such as 50 to 125 cps, for example about 75 to 100 cps.

According to a further aspect, the invention provides an aqueous composition for oral administration comprising ranitidine, or a pharmaceutically acceptable salt thereof, LCMT sucrose, ethanol, potassium dihydrogen orthophosphate and disodium hydrogen orthophosphate, peppermint flavouring, preservatives, viscosity enhancing agents, colouring aids, additional sweeteners, and mixtures thereof.

Ranitidine may be employed in the aqueous compositions according to the invention in the form of either its free base or a pharmaceutically acceptable salt. Such salts include salts with inorganic or organic acids such as the hydrochloride, hydrobromide, sulphate, acetate, maleate, succinate, citrate, tartrate, fumarate and acerbate salts. A particularly preferred salt of ranitidine is the hydrochloride.

Preferably the compositions according to the invention comprise ranitidine in the form of its hydrochloride.

Ranitidine may be employed in the aqueous compositions of the invention in encapsulated form which are described in, for example, EP349103, EP459695, EP473431, EP535937, EP538034, EP523847, WO92/21328, WO94/05260CA2068366, DE4333190, U.S. Pat. No. 5,084,278 and U.S. Pat. No. 5,607,697.

Preferably ranitidine and its salts are used in conventional form.

The aqueous compositions according to the invention are conveniently prepared in conventional manner, for example by mixing an aqueous solution of ranitidine, or a pharmaceutically acceptable salt thereof, together with ethanol, preservatives and flavouring with an aqueous solution or, or dispersion of the LCMT sucrose and buffer system followed by adjustment of pH.

The amount of ranitidine, preferably in the form of a pharmaceutically acceptable salt, particularly ranitidine hydrochloride, in the composition according to the invention is preferably in the range of 25 to 150 mg per dosage unit e.g. 75 mg, expressed as the weight of free base.

The dosage unit is conveniently 5 to 20 ml, for example 15 ml which is equivalent to three teaspoons or a tablespoon. Preferably, the aqueous compositions according to the invention contain 25 to 150 mg, e.g. 75 mg, ranitidine, expressed as the weight of free base, per 15 ml dose.

The unit dose (for example per 15 ml) may be administered up to, for example, 12 times a day depending upon the nature and severity of the conditions being treated, and the age and weight of the patient. Thus, for example, in the treatment of minor gastrointestinal disorders associated with excess acid secretion such as, for example, acid indigestion, over-indulgence of food or drink (e.g. alcoholic beverages), acid, stomach, sour stomach, waterbrash/regurgitation, heartburn, such as episodic heartburn, nocturnal heartburn, and meal-induced heartburn, gastritis and dyspepsia, a 25–150 mg dose of ranitidine, e.g. a 75 mg dose, expressed as the weight of free base, may be administered up to 12 times a day, for example 6 times a day, as and when required.

The following non-limiting example further illustrates the invention.

EXAMPLE 1

|  | % w/v |
| --- | --- |
| Ranitidine HCl | 0.56 |
| Sucrose LCMT | 45.0 |
| Ethanol | 4.75 |
| Propylparaben | 0.015 |
| Butylparaben | 0.0075 |
| Sodium chloride | 0.10 |
| Disodium hydrogen orthophosphate | Used to adjust pH to 7.1 |
| Potassium dihydrogen orthophosphate | 0.095 |
| Water | qs |

An aqueous solution of ranitidine hydrochloride, ethanol, the preservatives and flavouring was mixed with an aqueous solution of the LCMT sucrose (obtained from Domino Sugar, New York) and buffer system. The pH was adjusted using sodium dihydrogen orthophosphate and the mixture was made up to the final, volume with water.

What is claimed is:

1. An aqueous pharmaceutical composition for oral administration comprising ranitidine, or a pharmaceutically acceptable salt thereof, characterised in that the composition contains low color metal, turbidity (LCMT) sucrose.

2. An aqueous composition as claimed in claim 1 containing 30–60% w/v LCMT sucrose based on the complete formulation.

3. An aqueous composition as claimed in claim 2 containing 45% w/v LCMT sucrose based on the complete formulation.

4. An aqueous composition as claimed in claim 1 containing 4–5.5% w/v ethanol based on the complete formulation.

5. An aqueous composition as claimed claim 1 having a pH in the range 6.8 to 7.4.

6. An aqueous composition as claimed in claim 1 using ranitidine in the form of its hydrochloride salt.

7. An aqueous composition as claimed in claim 1 wherein the amount of ranitidine is 25–150 mg per 15 ml dose expressed as free base.

8. An aqueous composition as claimed in claim 1 wherein the amount of ranitidine is 75 mg per 15 ml dose expressed as free base.

* * * * *